United States Patent
Ross et al.

(10) Patent No.: US 7,116,157 B2
(45) Date of Patent: Oct. 3, 2006

(54) HIGH OUTPUT IMPEDANCE CURRENT SOURCE

(75) Inventors: Alexander S. Ross, Albany, NY (US); Gary J. Saulnier, East Greenbush, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 54 days.

(21) Appl. No.: 10/898,647

(22) Filed: Jul. 23, 2004

(65) Prior Publication Data

US 2005/0024099 A1 Feb. 3, 2005

Related U.S. Application Data

(60) Provisional application No. 60/491,615, filed on Jul. 31, 2003.

(51) Int. Cl.
*G05F 1/10* (2006.01)
*G05F 3/02* (2006.01)

(52) U.S. Cl. ........................ 327/538; 327/103
(58) Field of Classification Search ................ 327/538, 327/543, 103
See application file for complete search history.

(56) References Cited

U.S. PATENT DOCUMENTS 4,427,935 A * 1/1984 Bowden ..................... 323/280
4,451,779 A * 5/1984 Griep .......................... 323/312
5,319,345 A * 6/1994 Abe et al. .................... 338/201

FOREIGN PATENT DOCUMENTS

JP         63182719 A  *  7/1988

* cited by examiner

*Primary Examiner*—Quan Tra
(74) *Attorney, Agent, or Firm*—Notaro & Michalos PC

(57) ABSTRACT

A circuit for applications such as electrical impedance tomography includes a voltage-to-current converter having an input for receiving a voltage waveform and an output for outputting a current waveform to a load at an output resistance for the voltage-to-current converter. The voltage-to-current converter includes resistance control means for adjusting the output resistance of the voltage-to-current converter under computer control. The circuit of the present invention also includes an inductance control circuit operatively connected to the voltage-to-current converter for synthesizing a selected inductance. The inductance control circuit includes inductance control means for adjusting the value of the selected inductance by computer control. The operative connection between the voltage-to-current converter and the inductance control circuit causes application of the selected inductance to the output of the voltage-to-current converter so that an overall output impedance of the current source at the load is both high and controllable.

19 Claims, 7 Drawing Sheets

12

40

FIG. 6
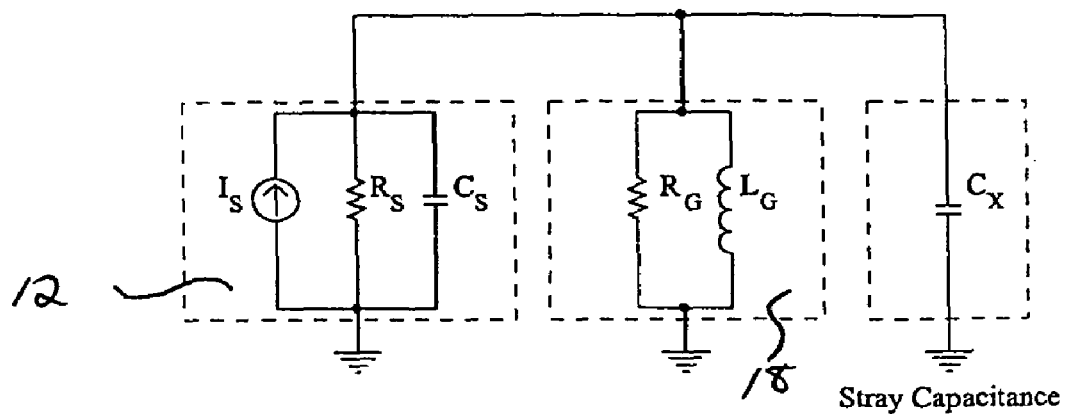
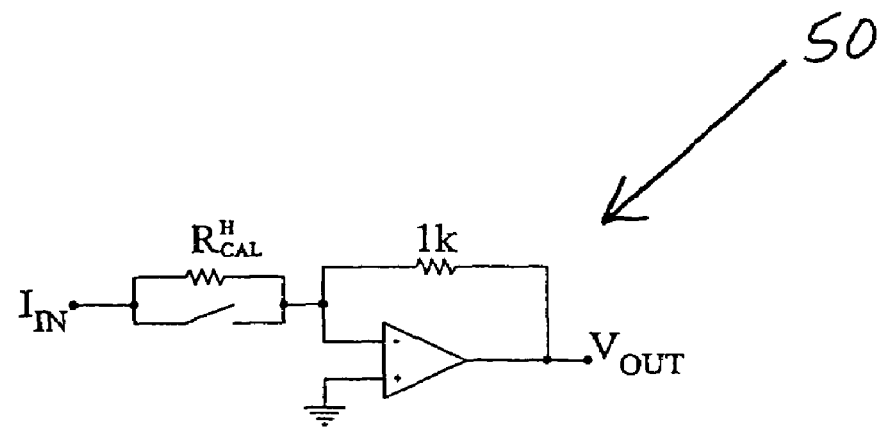
FIG. 7

HIGH OUTPUT IMPEDANCE CURRENT SOURCE

CROSS-REFERENCE TO RELATED APPLICATION

This application claims priority on U.S. Provisional Application 60/491,615, filed Jul. 31, 2003, which is incorporated here by reference.

STATEMENT OF GOVERNMENT INTEREST

The invention disclosed herein was developed partly by funds provided under NSF Award No. EEC-9986821.

FIELD AND BACKGROUND OF THE INVENTION

The present invention relates generally to the field of electrical impedance tomography (EIT), and in particular to new and useful circuits and calibration algorithms or techniques which permit highly precise current waveforms to be produced and introduced to various loads.

This invention was developed for use in electrical impedance imaging (also called electrical impedance tomography and electrical impedance spectroscopy) where the generation of current waveforms is needed for the purpose of diagnosing breast cancer and other disease.

It should be noted that other applications in electrical impedance imaging exist such as defect detection, geological imaging, and process monitoring. Likewise, the invention may be useful for applications other than electrical impedance imaging.

To obtain the data needed to reconstruct an electrical impedance image, current waveforms are applied to a load through electrodes, the voltages that appear on the electrodes are measured, and these data are processed by a reconstruction algorithm to generate a two or three-dimensional image of the interior conductivity and/or permittivity. The current waveforms are typically sinusoids with a frequency in the range of 100 Hz to 10 MHz. In a 32-electrode system, as many as 32 current sources may be used to apply currents to all the electrodes simultaneously. Each set of applied currents is called a current pattern.

The patterns of current that are applied (U.S. Pat. Nos. 4,920,490; 5,588,429; 5,381,333; 5,272,624), methods by which voltages are measured (U.S. Pat. No. 5,544,662) and the algorithms which reconstruct the images (U.S. Pat. Nos. 4,920,490; 5,284,142; 5,351,697; 5,390,110) have been previously described.

The quality of the images produced in impedance imaging depends greatly on the precision of the applied currents. Precision can be defined as the reciprocal of the fractional change in current resulting from a change in load impedance. High precision reflects little change in current while low precision reflects large change in current. The current sources must be able to provide the desired current over the range of load impedances presented by the electrodes. To achieve this precision, the current sources should have an output impedance that is much higher than the load impedances. Here, a new current source is described which improves the precision of the applied currents and expands the frequency range over which currents may be generated. To our knowledge, no current source presently exists which is capable of producing an output over the range of 100 Hz and 1 MHz with output impedances in the tens to hundreds of Megohms. This level of output impedance is required in order to achieve the level of precision necessary in an optimized, applied current, impedance imaging system.

SUMMARY OF THE INVENTION

It is an object of the present invention to enhance the precision of applied currents in EIT, such that the quality of images is improved.

It is another object of the present invention to provide a current source that is able to provide current with enhanced precision over the range of load impedances presented by electrodes.

It is a further object of the present invention to provide a current source having an output impedance that is much higher than load impedances.

It is yet another object of the present invention to provide a current source which expands the frequency range over which precise applied currents may be generated and produces an output between 100 Hz and 1 MHz with output impedances in the tens to hundreds of Megohms.

Accordingly, a high precision, multiple frequency, capacitance compensated current source is provided, which allows nearly independent adjustment of output resistance and output capacitance and output impedances in excess of 2 G$\Omega$ between 100 Hz and 1 MHz.

The precision of a current source depends on its output impedance relative to the load impedance it is expected to drive. For an ideal source, the output impedance is infinite so that all generated current flows to the load. In the case of a real (as opposed to theoretical) current source, a finite output impedance exists between the output terminals of the source which diverts some current from the intended load. The circuit of the present invention in combination with the calibration circuit and algorithm, has the ability to adjust its output impedance to values which are orders of magnitude higher than are presently available by any other circuit or method.

The circuit of the present invention is a current source which comprises a voltage-to-current converter having an input for receiving a voltage waveform and an output for outputting a current waveform to a load at an output impedance for the voltage-to-current converter. The voltage-to-current converter includes resistance control means for adjusting the output resistance of the voltage-to-current converter under computer control. The circuit of the present invention also includes an inductance control circuit operatively connected to the voltage-to-current converter for synthesizing a selected inductance. The inductance control circuit includes inductance control means for adjusting the value of the selected inductance by computer control. The operative connection between the voltage-to-current converter and the inductance control circuit causes application of the selected inductance to the output of the voltage-to-current converter so that an overall output impedance of the current source at the load is both high and controllable.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 6 is an electric circuit model for the complete current source of the present invention impedance converter topology used for output impedance adjustment;

FIG. 7 is an electric circuit diagram of the current-to-voltage converter used for current source calibration;

DESCRIPTION OF THE PREFERRED EMBODIMENTS

Figure 1:
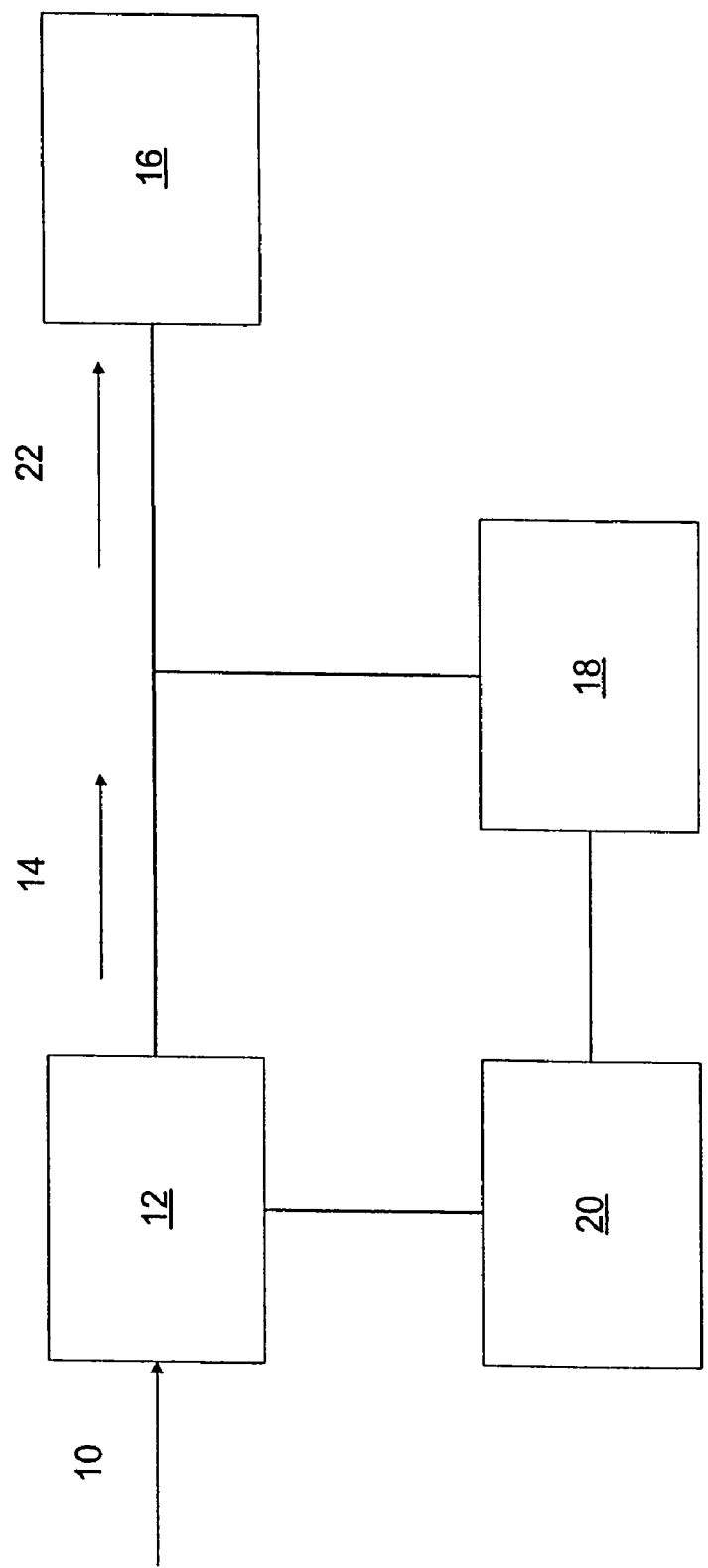
FIG. 1 is a block diagram of the invention.

Referring now to the drawings, in which like reference numerals are used to refer to the same or similar elements, FIG. 1 shows a block diagram of the invention. A voltage waveform 10 is fed into a voltage to current (V-I) converter 12 which produces an output current ($I_{OUT}$) 14. The output impedance of the V-I converter 12 can be adjusted using a computer 20. The output current 14 from the V-I converter 12 is fed to a load impedance 16. Also connected to the output of the V-I converter 12 and the input of the load impedance 16 is a generalized impedance converter (GIC) circuit 18 which can also be adjusted using computer 20. The object of the circuit is to produce a current in the load ($I_{LOAD}$) 22 that is proportional to the input voltage waveform 10 and which varies a minimal amount in response to changes in the value of the load impedance 16.

Figure 2:
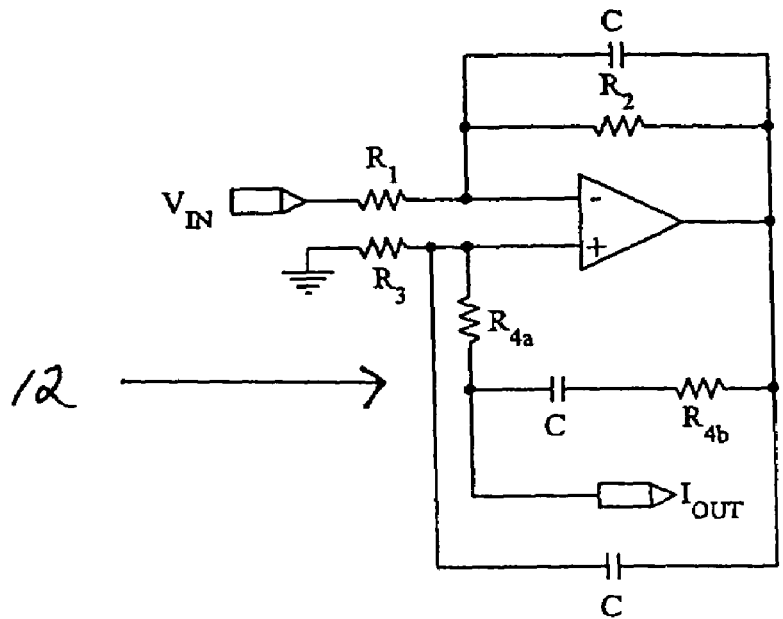
FIG. 2 is an electric circuit diagram of the modified enhanced Howland voltage-to-current converter topology used for current waveform generation.

As shown in FIG. 2, the V-I converter 12 is implemented as an enhanced Howland circuit, which has been modified to enable adjustment of the output impedance without changing the transconductance. The capacitors in the circuit are optional, with the capacitor located between resistors $R_{4a}$ and $R_{4b}$ being used prevent a DC current component from appearing in output current ($I_{OUT}$) 14 (replaced with a short if not used) and the other two capacitors being used to improve circuit stability (replaced with open circuits if not used). With an ideal operational amplifier the transconductance is the ratio of the output current to the input voltage. The transconductance of the source is a function of three resistors and is given by:

$$\frac{I_{OUT}}{V_{IN}} = \frac{R_2}{R_1 R_{4b}}. \quad (1)$$

The output resistance of this circuit can be adjusted by manipulating resistor $R_3$. This specific resistor is used to adjust output impedance as it does not affect the transconductance of the circuit (it does not appear in Equation 1). The output impedance for the circuit with an ideal operational amplifier is resistive. The expression for output resistance for this circuit is calculated by grounding the input terminal and connecting a voltage source to the output and finding the ratio of the applied voltage to the resulting current flowing into the output. The output resistance, assuming an ideal operational amplifier, is given by:

$$R_{OUT} = \frac{R_1 R_{4b}(R_3 + R_{4a})}{R_2 R_3 - R_1(R_{4a} + R_{4b})}. \quad (2)$$

Note that, due to the form of the denominator in Equation 2, the output resistance can be either negative or positive while proper selection of component values can produce an infinite output resistance.

Figure 3:
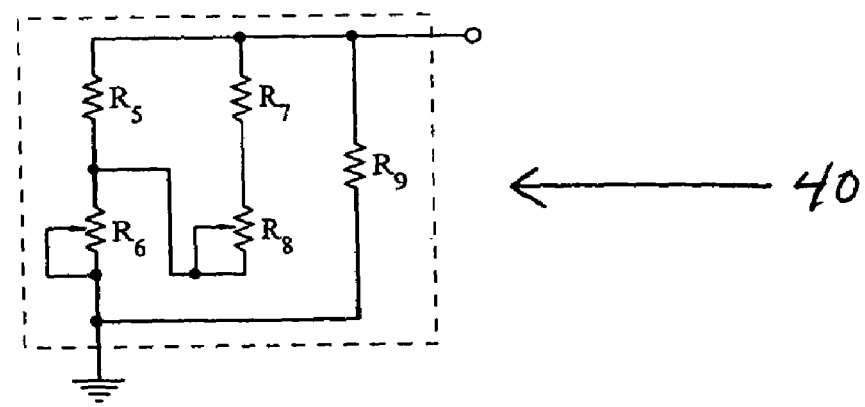
FIG. 3 is an electric circuit diagram which shows the resistor network used for the Howland circuit and Generalized Impedance Converter (GIC) resistive element adjustment.

To enable automated adjustment of $R_{OUT}$, the resistive element $R_3$ in the Howland source is implemented as a network 40 of fixed resistors and digitally-controlled potentiometers as shown in FIG. 3. This network 40 permits coarse resistance adjustment using digital potentiometer $R_6$, fine resistance adjustment using digital potentiometer $R_8$, selection of the coarse adjustment range using fixed resistor $R_5$, selection of the fine adjustment range using fixed resistor $R_7$, and adjustment of the adjustment center-point using fixed resistor $R_9$. The resistance of this network 40 is given by:

$$R_3 = \frac{R_5 R_7 R_9 + R_5 R_8 R_9 + R_5 R_6 R_9 + R_6 R_7 R_9 + R_6 R_8 R_9}{R_5 R_7 + R_5 R_8 + R_5 R_6 + R_6 R_7 + R_6 R_8 + R_5 R_9 + R_7 R_9 + R_8 R_9}. \quad (3)$$

Based on the equations above, which assume an ideal operational amplifier, it would be possible to adjust $R_3$ to obtain infinite output resistance and, therefore, infinite output impedance for the Howland source. However, when the circuit is implemented using a real operational amplifier, an output capacitance appears in parallel with the output resistance. This capacitance introduces a reactive component into the output impedance and results in finite output impedance even if the output resistance is made infinite. The presence of this capacitance limits the output impedance to be below the optimal levels desired for electrical impedance imaging.

To increase the output impedance in the presence of non-zero output capacitance, a generalized impedance converter (GIC) 18 (also referred to in the literature as a gyrator or Riordan circuit) is used to synthesize an inductance which is attached to the output of the Howland circuit. The synthesized inductance compensates for the output and stray capacitance by producing an equivalent RLC parallel resonant circuit, where R is the total parallel resistance, L is the synthesized inductance and C is the total parallel capacitance. For such a parallel RLC circuit, the equivalent impedance is given by:

$$Z_{EQ} = R \left\| \frac{1}{sC} \right\| sL \quad (4)$$

$$= \frac{-j\omega RL(R - \omega^2 RLC) + \omega^2 L^2 R}{(R - \omega^2 RLC)^2 + (\omega L)^2}. \quad (5)$$

Selecting the inductance L to produce resonance at the operating frequency, i.e.

$$\omega = \frac{1}{\sqrt{LC}}, \quad (6)$$

results in an equivalent impedance of $$Z_{EQ} = R \quad (7)$$

indicating that the effect of the capacitance, C, is nullified.

Figure 4:
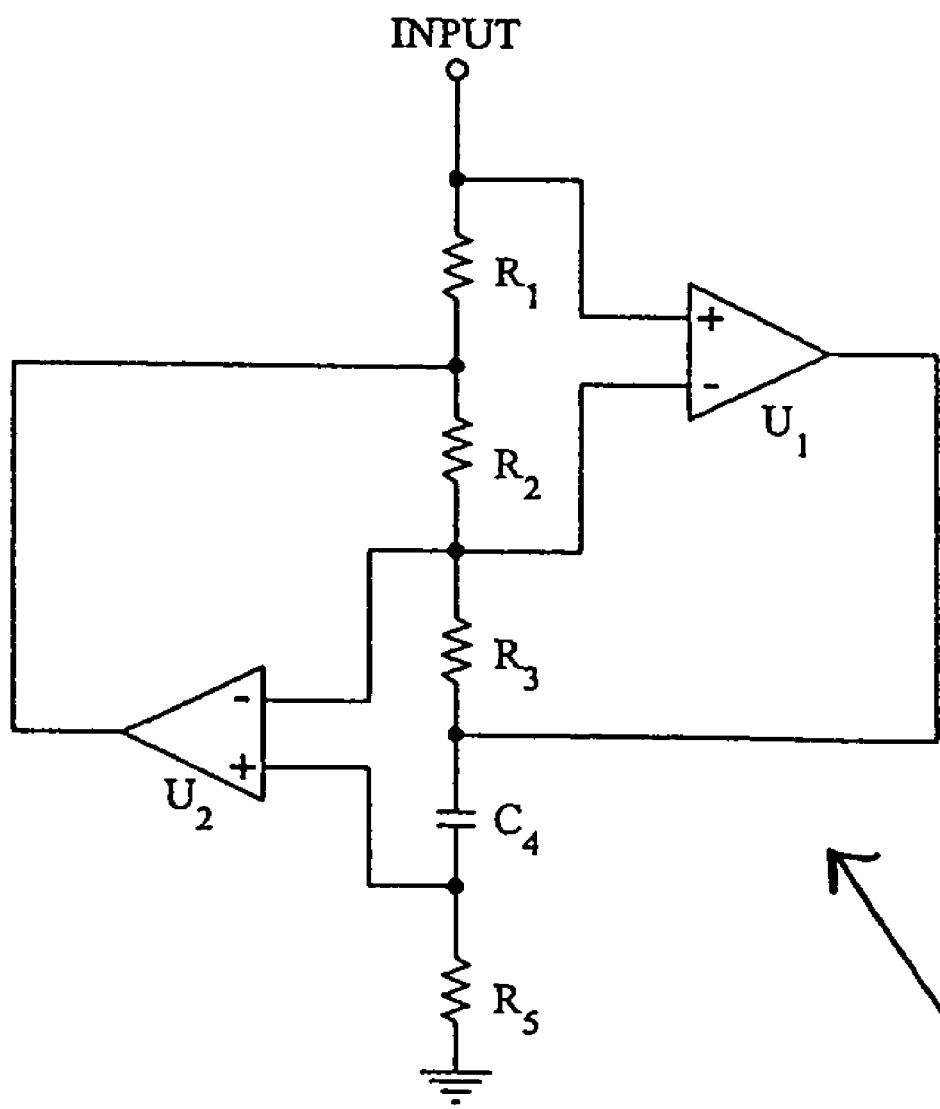
FIG. 4 is an electric circuit diagram showing the basic topology of the generalized impedance converter configured to synthesize an inductance.

While several GIC implementations exist, the topology shown in FIG. 4 is used for its excellent stability characteristics, its ability to synthesize a high-Q inductance and excellent performance characteristics at high frequencies. For ideal operational amplifiers, the synthesized inductance of the GIC circuit 18 is given by:

$$L = \frac{R_1 R_3 R_5 C_4}{R_2}. \quad (8)$$

When constructed using real operational amplifiers, the GIC 18 will produce an impedance that can be modeled as the inductance of Equation 8 in parallel with a resistance.

Figure 5:
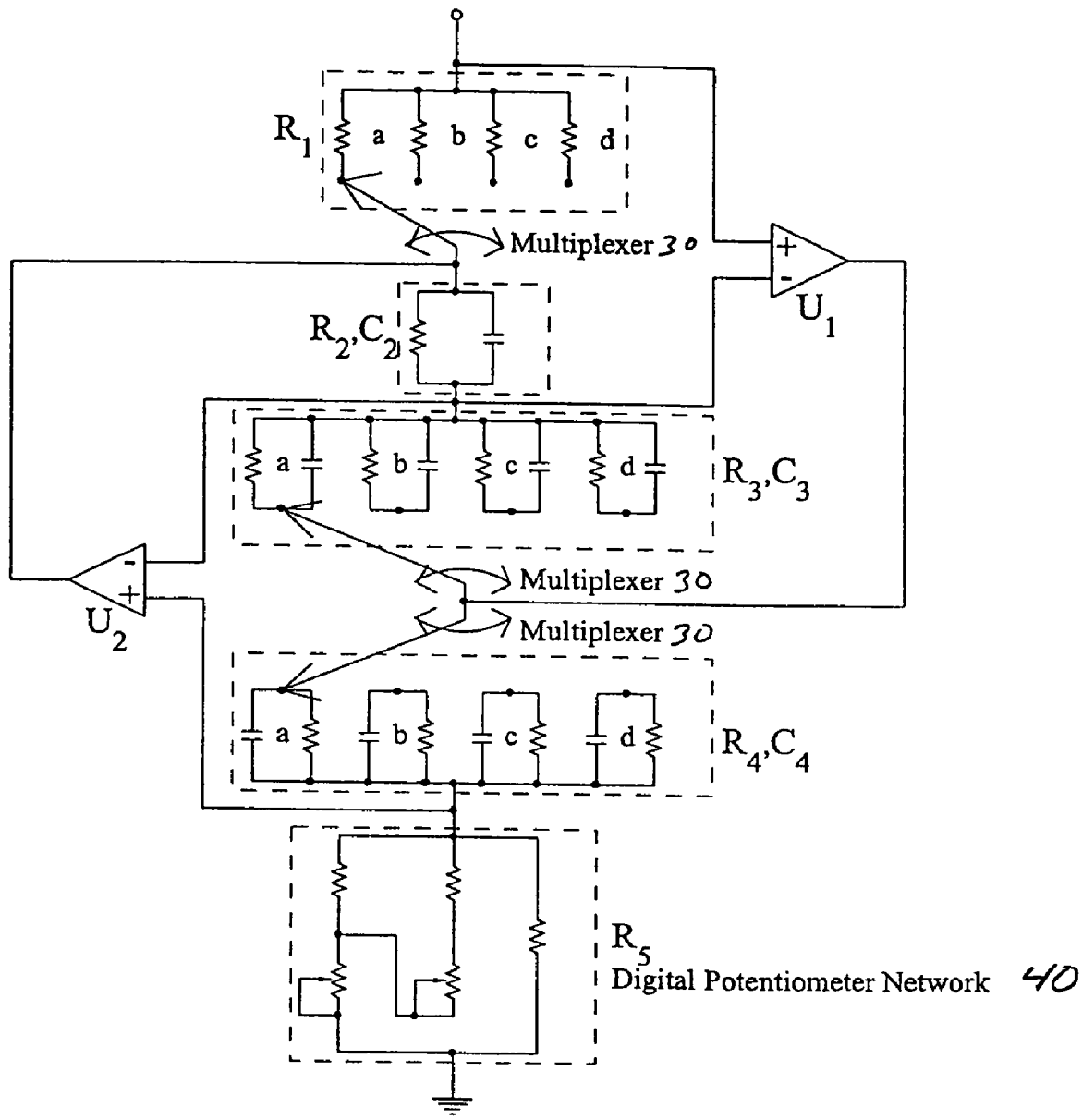
FIG. 5 is an electric circuit diagram which shows the generalized impedance converter topology configured to synthesize an inductance for output impedance adjustment.

As indicated by Equation 6, the inductance needed to compensate for a given capacitance is a function of frequency. To provide compensation over a large range of frequencies requires a large range of inductor values. Therefore, in practice, this GIC circuit 18 can be modified to enable the synthesis of the inductances needed for multiple discrete frequencies of operation over a broad frequency range. FIG. 5 shows one example of how multiplexers 30 can be used to select elements $R_1$, $R_3$, and $C_4$ from banks of elements. By the appropriate selection of the resistors and capacitors in the banks, the synthesized inductance can be made to vary over orders of magnitude with operating frequency. To provide stability in the presence of large, capacitive loads, and to compensate for the addition of capacitance due to the multiplexers 30, elements $R_2$, $R_3$, and $C_4$ are replaced by resistor/capacitor parallel pairs. In the case of $C_4$, the addition of a parallel resistance provides a DC pathway that prevents a DC voltage from accumulating across $C_4$. In the case of $R_2$ and $R_3$, the addition of a parallel capacitance improves the stability of the circuit by modifying the feedback paths of the operational amplifiers in a way that increases the phase margin. Automatic adjustment of the synthesized inductance via computer control is achieved by using the resistor and digital potentiometer network 40 topology shown in FIG. 3 in place of $R_5$. Operation and description of this network 40 is the same as in the current source.

When the Howland source and GIC 18 are placed in parallel as in FIG. 1, adjustment of the digital potentiometers permits nearly independent adjustment of output resistance and total (sum of output and stray) capacitances. As noted above, nonidealities associated with the active devices in the GIC 18 results in a resistance being synthesized in parallel with the desired inductance. The output resistance of the Howland source, which can be made positive or negative, is adjusted to compensate for this GIC 18 resistance. A model for the complete current source is shown in FIG. 6. Here the output resistance and capacitance of the Howland source are denoted by $R_S$ and $C_S$, respectively, and the ideal current source output (i.e. the current that the source would provide if driving a short circuit) is denoted by $I_S$. The inductance synthesized by the GIC 18 is denoted by $L_G$ while the resistance produced is denoted by $R_G$. Additional stray capacitance is denoted by $C_X$. Adjustment of the digital potentiometers in the Howland source allows the variation of $R_S$ with only small variation in $C_S$. Likewise, adjustment of the digital potentiometers and multiplexers 30 in the GIC 18 allows the variation of $L_G$ with only small variation in $R_G$. The equivalent resistance of the parallel circuit is $$R_{EQ} = \frac{R_S R_G}{R_S + R_G} \quad (9)$$

and setting $R_S = -R_G$ produces the desired infinite output resistance. Based on Equation 6, setting $$L_G = \frac{1}{\omega^2 (C_S + C_X)} \quad (10)$$

results in the effective cancellation of the capacitance. In practice, the output impedance adjustment is limited by the finite adjustment resolution of the digital potentiometers used for the adjustment of resistances in the Howland source and in the GIC 18.

The output current from the current source is measured and the output impedance adjustment process is guided by attaching a current to voltage (I-V) converter 50 (FIG. 7) in place of the load impedance. When the switch in FIG. 7 is closed, the circuit ideally presents a virtual ground to the driving circuit. The virtual ground means that the voltage is held at ground potential but current does not flow directly to ground. The current delivered to this virtual ground flows through the 1 kΩ resistance and produces an output voltage $$V_{OUT} = -1000 I_{IN}. \quad (11)$$

Since the current is being driven into a ground potential, no current flows in the output impedance of the current source and, measurement of this $V_{OUT}$ allows the determination of the ideal current source output ($I_S$ in FIG. 6) even if the output impedance is finite.

To measure the current source output impedance, and guide the adjustment of the digital potentiometers to maximize its value, the output voltage of the I-V converter 50 is measured using a phase-sensitive voltmeter, once with the switch closed and another with it open. The phase-sensitive voltmeter measures complex voltage with the phase referenced to that of the voltage waveform 10. Opening the switch results in the circuit presenting a load resistance of $R_{CAL}^H$. Using the known value of $R_{CAL}^H$, the output resistance ($R_{OUT}$) and capacitance ($C_{OUT}$) of the source are calculated using Equations 12 and 13, where V is a voltage measurement with subscript R indicating an in-phase (real) value, subscript Q indicating a quadrature (imaginary) value, superscript H indicating that the I-V converter 50 is configured with the switch open $R_{CAL}^H$ in place), and superscript L indicating that the I-V converter 50 is configured with the switch closed (0Ω load) in place. The angular operating frequency is given by ω, and $R_{CAL}^H$ is the value of the load resistor in the I-V converter 50. The adjustment procedure is iterative. Once voltage measurements are made, $R_{OUT}$ and $C_{OUT}$ are computed and the digital potentiometers are adjusted in a direction to increase $R_{OUT}$ and decrease $C_{OUT}$. This adjustment and measurement procedure is repeated until the maximum obtainable output impedance or an output impedance above a predefined level is obtained.

$$R_{OUT} = \frac{(V_Q^H)^2 + (V_R^H)^2}{V_Q^L V_Q^H + V_R^L V_R^H - (V_R^H)^2 - (V_Q^H)^2} R_{CAL}^H \quad (12)$$

$$C_{OUT} = \frac{V_Q^L V_R^H - V_R^L V_Q^H}{((V_Q^H)^2 + (V_R^H)^2)\omega R_{CAL}^H} \quad (13)$$

Figure 8:
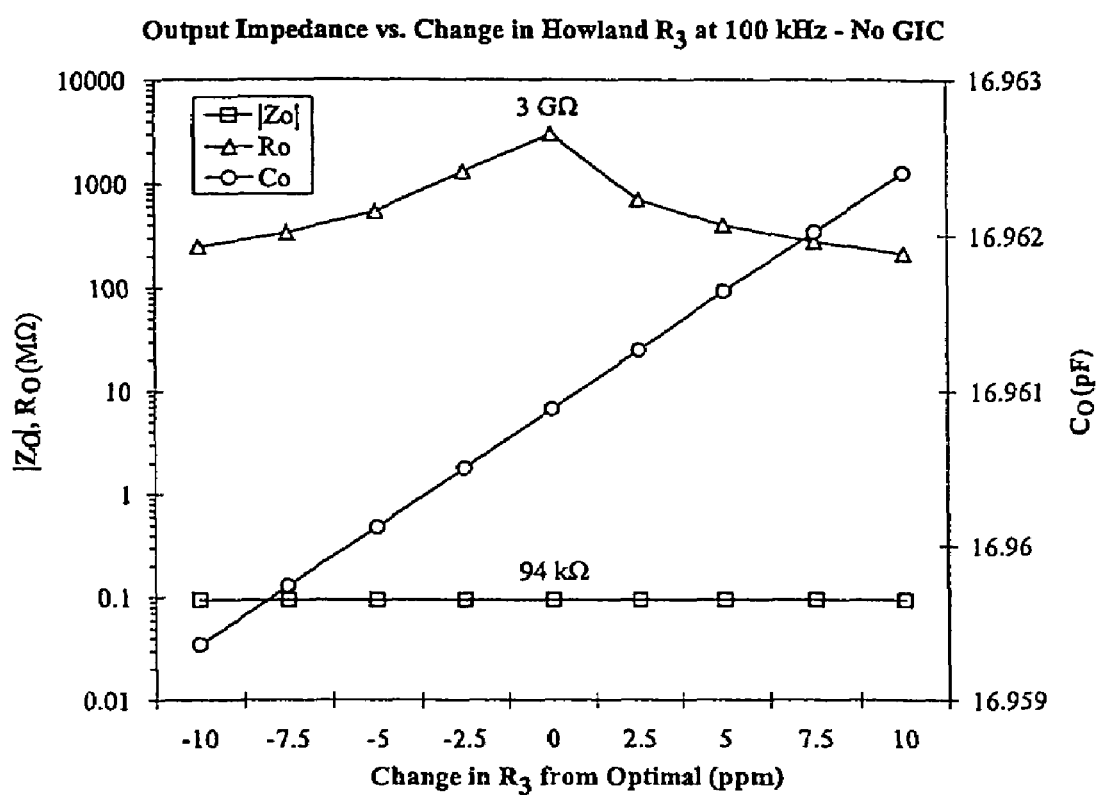
FIG. 8 is a plot of output impedance versus the change in the Howland source R3 at 100 kHz without the GIC.
Figure 9:
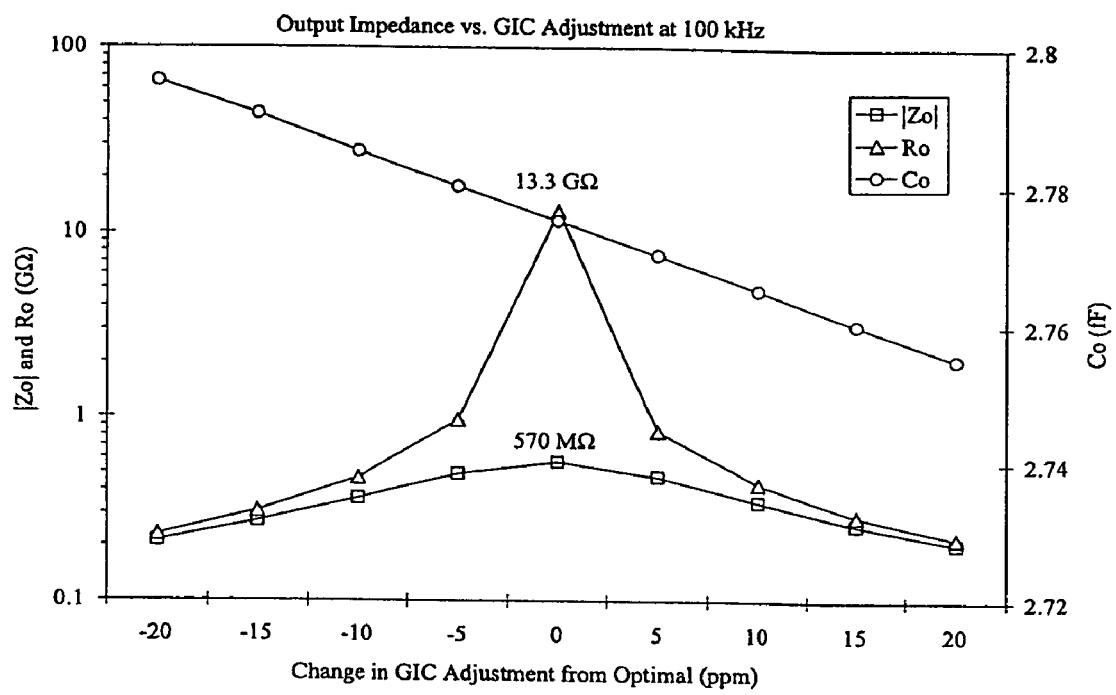
FIG. 9 is a plot of output impedance versus the change in the Howland source R3 at 100 kHz as a result of GIC adjustment.

An example of the increase in output impedance can be seen by comparing FIG. 8 to FIG. 9. FIG. 8 shows simulated data of the Howland source prior to the addition of the GIC 18. Although the output resistance can be tuned quite high, output capacitance prevents the overall output impedance from reaching high values. FIG. 9 shows the simulated data of the complete current source output impedance after the GIC 18 is added to the Howland source, and the overall circuit is adjusted. With output capacitance and resistance adjusted, the overall output impedance is now orders of magnitude higher than before the addition of the GIC 18. FIG. 8 shows a maximum output impedance of 94 kΩ at 100 kHz, while after implementing and adjusting the GIC 18, a maximum output impedance of 570 MΩ was reached at the same frequency.

While a specific embodiment of the invention has been shown and described in detail to illustrate the application of the principles of the invention, it will be understood that the invention may be embodied otherwise without departing from such principles.

What is claimed is:

1. A current source comprising:
   a voltage-to-current converter having an input for receiving a voltage waveform and an output for outputting a current waveform to a load at an output impedance for the voltage-to-current converter, the voltage-to-current converter including resistance control means for adjusting the output resistance of the voltage-to-current converter under computer control, an output resistance being high with respect to the magnitude of an impedance of the load and the output impedance having a non-zero output and stray capacitance; and
   an inductance synthesis circuit operatively connected to the output of the voltage-to-current converter for synthesizing a selected inductance, the inductance synthesis circuit including inductance control means for adjusting and controlling the value of the selected inductance to a level to cancel the contribution of the output and stray capacitance to the output impedance of the voltage-to-current converter at a selected operating frequency, the inductance synthesis circuit causing application of the selected inductance to the output of the voltage-to-current converter so that an overall output impedance of the current source at the load is high and controllable.

2. A current source according to claim 1, wherein the voltage-to-current converter is a Howland circuit.

3. A current source according to claim 1, wherein the output resistance can be adjusted without changing transconductance.

4. A current source according to claim 1, wherein the output resistance is adjusted via a resistive network comprising fixed and adjustable resistors.

5. A current source according to claim 4, wherein adjustable resistors are used for coarse resistance adjustment and fine resistance adjustment.

6. A current source according to claim 4, wherein fixed resistors are used for selection of a coarse adjustment range, selection of a fine adjustment selection, and selection of a centerpoint around which range adjustments are made.

7. A current source according to claim 2, wherein the inductance control circuit is a generalized impedance converter.

8. A current source according to claim 7, wherein the generalized impedance converter includes at least one multiplexer for selecting impedances.

9. A current source according to claim 8, wherein the Howland circuit and the generalized impedance converter both include a computer controlled potentiometer.

10. A current source according to claim 9, wherein each computer controlled potentiometer is a digital potentiometer.

11. A current source comprising:
    a voltage-to-current converter comprising a Howland circuit and having an input for receiving a voltage waveform and an output for outputting a current waveform to a load at an output impedance for the voltage-to-current converter, the voltage-to-current converter including resistance control means for adjusting the output resistance of the voltage-to-current converter under computer control; and
    an inductance control circuit operatively connected to the voltage-to-current converter for synthesizing a selected inductance, the inductance control circuit including inductance control means for adjusting the value of the selected inductance, the inductance control circuit causing application of the selected inductance to the output of the voltage-to-current converter so that an overall output impedance of the current source at the load is both high and controllable.

12. A current source according to claim 11, wherein the output resistance is adjusted without changing transconductance.

13. A current source according to claim 11, wherein the output resistance is adjusted via a resistive network comprising fixed and adjustable resistors.

14. A current source according to claim 13, including adjustable resistors in the resistance control means for coarse resistance adjustment and fine resistance adjustment.

15. A current source according to claim 13, including fixed resistors in the resistance control means for selection of a coarse adjustment range, selection of a fine adjustment selection, and selection of a centerpoint around which range adjustments are made.

16. A current source according to claim 11, wherein the inductance control circuit is a generalized impedance converter.

17. A current source according to claim 16, wherein the generalized impedance converter includes at least one multiplexer for selecting impedances.

18. A current source according to claim 17, wherein the Howland circuit and the generalized impedance converter both include a computer controlled potentiometer.

19. A current source according to claim 18, wherein each computer controlled potentiometer is a digital potentiometer.

* * * * *